(12) United States Patent
Bostick et al.

(10) Patent No.: US 10,181,333 B2
(45) Date of Patent: Jan. 15, 2019

(54) INTELLIGENT TRUTHFULNESS INDICATOR ASSOCIATION

(71) Applicant: International Business Machines Corporation, Armonk, NY (US)

(72) Inventors: James E. Bostick, Cedar Park, TX (US); John M. Ganci, Jr., Cary, NC (US); Sarbajit Rakshit, Kolkata (IN); Gandhi Sivakumar, Victoria (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/478,263

(22) Filed: Apr. 4, 2017

(65) Prior Publication Data

US 2018/0286429 A1  Oct. 4, 2018

(51) Int. Cl.
*G10L 17/26* (2013.01)
*G06Q 50/22* (2018.01)
(Continued)

(52) U.S. Cl.
CPC ............ *G10L 25/63* (2013.01); *A61B 5/0205* (2013.01); *G06F 17/2775* (2013.01);
(Continued)

(58) Field of Classification Search
CPC .................................................. G06Q 10/10
See application file for complete search history.

(56) References Cited

U.S. PATENT DOCUMENTS 5,853,005 A * 12/1998 Scanlon ................ A61B 5/113
600/459
9,055,071 B1   6/2015 Gates et al.
(Continued)

FOREIGN PATENT DOCUMENTS

CN       103040477 A  *  4/2013
CN       104545950 A  *  4/2015

OTHER PUBLICATIONS

Z. Inanoglu, et al., "Emotion Conversion using F0 Segment Selection," Interspeech, 2008.
(Continued)

*Primary Examiner* — Shreyans A Patel
(74) *Attorney, Agent, or Firm* — Christopher McLane; George S. Blasiak; Heslin Rothenberg Farley & Mesiti PC

(57) ABSTRACT

Methods, computer program products, and systems are presented. The method computer program products, and systems can include, for instance: obtaining speech based message data and biometric data of a speaker user of a messaging system, the speech based message data being input into a computer device by the speaker user and the biometric data indicating one or more aspect of a physical condition of the speaker user during the input of the speech based message data into the computer device; processing data to determine a truthfulness parameter of the speech based message data, the processing data to determine a truthfulness parameter including processing the biometric data; and associating the truthfulness parameter to the speech based message data, wherein the associating includes tagging the speech based message data with the truthfulness parameter.

19 Claims, 7 Drawing Sheets

(51) Int. Cl.
*G10L 25/63* (2013.01)
*G06F 17/27* (2006.01)
*A61B 5/0205* (2006.01)
*A61B 5/021* (2006.01)
*A61B 5/024* (2006.01)
*A61B 5/08* (2006.01)
*A61B 5/053* (2006.01)

(52) U.S. Cl.
CPC ............... *A61B 5/021* (2013.01); *A61B 5/024* (2013.01); *A61B 5/053* (2013.01); *A61B 5/08* (2013.01)

(56) References Cited

U.S. PATENT DOCUMENTS

| | | | | |
|---|---|---|---|---|
| 2009/0116703 | A1* | 5/2009 | Schultz | G06F 21/32 382/118 |
| 2009/0140864 | A1* | 6/2009 | Aaron | G06Q 30/02 340/573.1 |
| 2011/0182481 | A1* | 7/2011 | Dernis | G06K 9/00892 382/116 |
| 2012/0035906 | A1* | 2/2012 | Jephcott | G06F 17/289 704/2 |
| 2013/0151240 | A1* | 6/2013 | Myslinski | G06F 17/20 704/9 |
| 2015/0271111 | A1 | 9/2015 | Dowdell | |
| 2016/0057565 | A1* | 2/2016 | Gold | H04L 67/12 455/41.1 |
| 2016/0196339 | A1 | 7/2016 | Myslinski | |
| 2017/0018007 | A1* | 1/2017 | DeFrank | G06Q 30/0262 |

OTHER PUBLICATIONS

Unknown, "Speech Synthesis," Wikipedia https://en.wikipedia.org/w/index.php?title=Speech_synthesis&oldid=749965374, , last updated Nov. 17, 2016.
IBM, "Tone Analyzer," http://www.ibm.com/watson/developercloud/tone-analyzer.html, 2016.
V. Francisco, et al., "Exploring the Compositionality of Emotions in Text: Word Emotions, Sentence Emotions, and Automated Tagging," American Association for Artificial Intelligence (www.aaai.org), 2006.
S. Shivhare, et al., "Emotion Detection from Text," arXiv preprint arXiv:1205.4944 (2012).

* cited by examiner

INTELLIGENT TRUTHFULNESS INDICATOR ASSOCIATION

BACKGROUND

Natural Language Processing (NLP) is a form of artificial intelligence including a variety of researched disciplines. Speech Recognition can involve processing a sound sample of a person or people speaking, and determining the textual representation of the speech. In natural speech there minimal pauses between successive words, and thus speech segmentation can be included in a speech recognition process. In most spoken languages, the sounds representing successive letters blend into each other in a process termed coarticulation, so the conversion of the analog signal to discrete characters can present challenges. Sentiment analysis can involve extracting subjective information from a speech sample or text string, sometimes using external sources to determine "polarity" about specific objects, i.e. whether the text string has a positive polarity or negative polarity. Sentiment analysis can be non-polar and include detection of sentiments such as "fear" "anger" "sadness" "happiness" and "disgust."

SUMMARY

Shortcomings of the prior art are overcome, and additional advantages are provided, through the provision, in one aspect, of a method. The method can include, for example: obtaining speech based message data and biometric data of a speaker user of a messaging system, the speech based message data being input into a computer device by the speaker user and the biometric data indicating one or more aspect of a physical condition of the speaker user during the input of the speech based message data into the computer device; processing data to determine a truthfulness parameter of the speech based message data, the processing data to determine a truthfulness parameter including processing the biometric data; and associating the truthfulness parameter to the speech based message data, wherein the associating includes tagging the speech based message data with the truthfulness parameter.

In another aspect, a computer program product can be provided. The computer program product can include a computer readable storage medium readable by one or more processing unit and storing instructions for execution by one or more processor for performing a method. The method can include, for example: obtaining speech based message data and biometric data of a speaker user of a messaging system, the speech based message data being input into a computer device by the speaker user and the biometric data indicating one or more aspect of a physical condition of the speaker user during the input of the speech based message data into the computer device; processing data to determine a truthfulness parameter of the speech based message data, the processing data to determine a truthfulness parameter including processing the biometric data; and associating the truthfulness parameter to the speech based message data, wherein the associating includes tagging the speech based message data with the truthfulness parameter.

In a further aspect, a system can be provided. The system can include, for example a memory. In addition, the system can include one or more processor in communication with the memory. Further, the system can include program instructions executable by the one or more processor via the memory to perform a method. The method can include, for example: obtaining speech based message data and biometric data of a speaker user of a messaging system, the speech based message data being input into a computer device by the speaker user and the biometric data indicating one or more aspect of a physical condition of the speaker user during the input of the speech based message data into the computer device; processing data to determine a truthfulness parameter of the speech based message data, the processing data to determine a truthfulness parameter including processing the biometric data; and associating the truthfulness parameter to the speech based message data, wherein the associating includes tagging the speech based message data with the truthfulness parameter.

Shortcomings of the prior art are overcome, and additional advantages are provided, through the provision, in one aspect, of a method. The method can include, for example: obtaining message data input into a messaging system by a user; processing the message data to determine a truthfulness parameter of the message data, the truthfulness parameter indicating a truthfulness of the message data; and associating the truthfulness parameter to the message data.

In another aspect, a computer program product can be provided. The computer program product can include a computer readable storage medium readable by one or more processing unit and storing instructions for execution by one or more processor for performing a method. The method can include, for example: obtaining message data input into a messaging system by a user; processing the message data to determine a truthfulness parameter of the message data, the truthfulness parameter indicating a truthfulness of the message data; and associating the truthfulness parameter to the message data.

In a further aspect, a system can be provided. The system can include, for example a memory. In addition, the system can include one or more processor in communication with the memory. Further, the system can include program instructions executable by the one or more processor via the memory to perform a method. The method can include, for example: obtaining message data input into a messaging system by a user; processing the message data to determine a truthfulness parameter of the message data, the truthfulness parameter indicating a truthfulness of the message data; and associating the truthfulness parameter to the message data.

Additional features are realized through the techniques set forth herein. Other embodiments and aspects, including but not limited to methods, computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
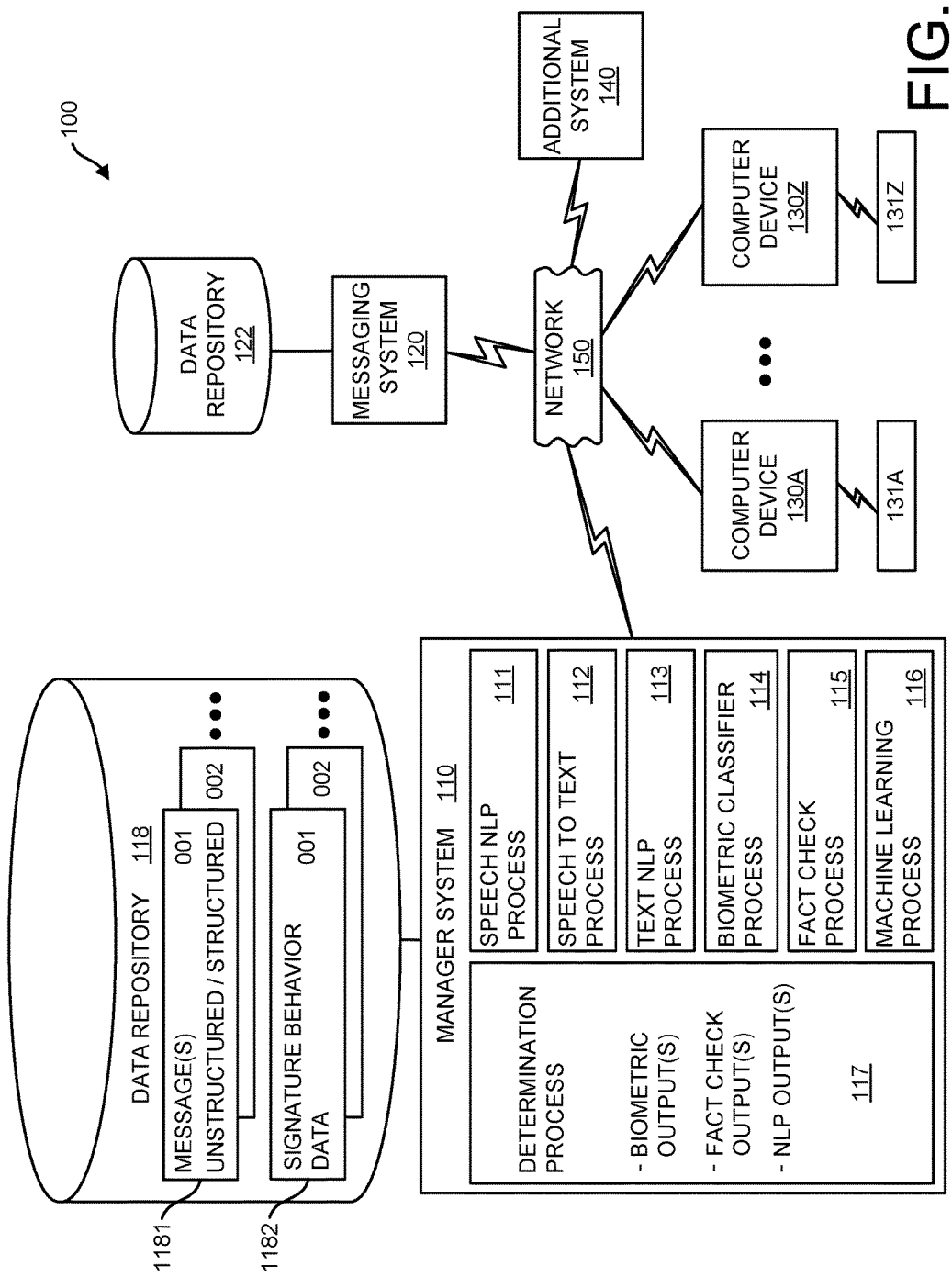
FIG. 1 depicts a system having manager system and a messaging system in one embodiment.

FIG. 1 is a block diagram of a system 100, in accordance with an embodiment as set forth herein. In the embodiment of FIG. 1, system 100 includes numerous devices, which may be or include computing nodes 10 as described herein, connected by a network 150. For example, network 150 may be a physical network or a virtual network. A physical network can be, for example, a physical telecommunications network connecting numerous computer nodes or systems, such as computer servers and computer clients. By contrast a virtual network can, for example, combine numerous physical networks or parts thereof into a logical virtual network. In another example, numerous virtual networks can be defined over a single physical network.

By way of explanation, FIG. 1 depicts an example environment. In one embodiment, system 100 can include a manager system 110, messaging system 120 one or more user computer device 130A-130Z and one or more additional system 140. Each of the different user computer devices 130A-130Z can be associated to a different user. User history data can be stored in data repository 122 of messaging system 120. In one embodiment system 100 can include one or more messaging system in addition to messaging system 120. In one embodiment manager system 110 can be external to messaging system 120 and to each of the one or more user computer device 130A-130Z. In one embodiment manager system 110 can be co-located with messaging system 120 or another messaging system. In one embodiment manager system 110 can be co-located with one or more user computer device 130A-130Z. In one embodiment each of manager system 110 and each computer device of one or more computer device 130A-130Z can be a computing node based system having one or more computing node, and manager system 110 can be external to and remote from and each computer device of one or more computer device 130A-130Z.

Regarding one or more user computer device 130A-130Z, a computer device of one or more user computer device 130A-130Z in one embodiment can include a computing node 10 provided by a client computer, e.g. a mobile device, e.g. a smartphone, smartwatch, tablet, or laptop or PC that runs one or more program including a web browser for browsing web pages and one or more program for support of communication with messaging system 120. Computer devices 130A-130Z can have respective associated computer devices 131A-131Z. Associated computer devices 131A-131Z associated to computer devices 130A-130Z can have respective users in common or to the respective users of computer device 130A-130Z. On one embodiment associated computer devices 131A-131Z can be provided by wearable computer devices e.g. smartwatch wearable computer devices. In some embodiments for persistent output of biometric data biometric sensors can be incorporated in computer devices 131A-131Z provided by wearable computer device that are adapted to remain in persistent proximity with a body of the user.

With further reference to FIG. 1, manager system 110 in one embodiment can run a speech NLP process 111 a speech to text process 112, a text natural language processing (NLP) process 113, a biometric classifier process 114, a fact check process 115, a machine learning process 116, and a truthfulness determining process 117.

Manager system 110 can include an associated data repository 118. Data repository 118 can include such data as a history of messages (e.g. speech and/or text based) of each of the plurality of users 001, 002. Stored messages of repository 118 can be in unstructured form (e.g. raw messages) or structured form (in a form after performing processing such as natural language processing (NLP)). Data repository can also store data obtained from one or more additional system 140 by activation of fact check process 115. In one embodiment, speech NLP process 111 can classify segments of speech into sentiments, speech to text process 112 can convert spoken words of speech based messages to text to facilitate further processing by text NLP process 113. Text NLP process 113 can parse and segment incoming text (original text messages or converted from a speech based message). Text NLP process 113 can classify messages or segments of messages into sentiments. Machine learning process 114 can perform machine learning to aid in truthfulness determinations performed by truthfulness determining process 117.

Sentiment analysis can determine the attitude of a speaker or a writer with respect to some topic or the overall contextual polarity of a speech or text sample. The attitude may be the speaker or writer's judgment or evaluation, affective state (that is to say, the emotional state of the speaker or writer when writing), or the intended emotional communication (that is to say, the emotional effect the speaker or writer wishes to have on the reader).

In one embodiment, speech NLP process 111 can classify speech samples into sentiments.

Speech NLP process 111 can use acoustic characteristics of emotions to classify speech samples into sentiment classification. Acoustic characteristics of different sentiments indicating emotions as summarized Murray & Arnott (1993) are presented herein below in Table A.

TABLE A

|  | Fear | Anger | Sadness | Happiness | Disgust |
| --- | --- | --- | --- | --- | --- |
| Speech Rate | Much Faster | Slightly Faster | Slightly Slower | Faster or Slower | Very Much Slower |
| Pitch Average | Very Much Higher | Very Much Higher | Slightly Lower | Much Higher | Very Much Lower |
| Pitch Range | Much Wider | Much Wider | Slightly Narrower | Much Wider | Slightly Wider |
| Intensity | Normal | Higher | Lower | Higher | Lower |
| Voice Quality | Irregular Voicing | Breathy Chest Tone | Resonant | Breathy Blaring | Grumbled Chest Tone |

TABLE A-continued

|  | Fear | Anger | Sadness | Happiness | Disgust |
|---|---|---|---|---|---|
| Pitch Changes | Normal | Abrupt On Stressed Syllables | Downward Inflection | Smooth Upward Inflections | Wide Downward Terminal Inflections |
| Articulation | Precise | Tense | Slurring | Normal | Normal |

Text NLP process 113 can perform sentiment analysis on incoming text (converted from speech or original text). In one embodiment text sentiment analysis can classify the polarity of a given text at the document, sentence, or feature/aspect level—whether the expressed opinion in a document, a sentence or an entity feature/aspect is positive, negative, or neutral. Advanced sentiment classification can classify beyond a polarity of a given text. Advanced sentiment classification can classify emotional states such as "fear" "anger" "sadness" "happiness" and/or "disgust".

In one embodiment, determining sentiment can include use of a scaling system whereby words commonly associated with having a negative, neutral or positive sentiment with them are given an associated number on a −10 to +10 scale (most negative up to most positive). Accordingly, it can be possible to adjust the sentiment of a given term relative to its environment (usually on the level of the sentence). When a piece of unstructured text is analyzed using natural language processing, each concept in the specified environment can be given a score based on the way sentiment words relate to the concept and its associated score. Accordingly, it can be possible to adjust the sentiment value of a concept relative to modifications that may surround it. Words, for example, that intensify, relax or negate the sentiment expressed by the concept can affect its score. Alternatively, texts can be given a positive and negative sentiment strength score if the goal is to determine the sentiment in a text rather than the overall polarity and strength of the text.

Performing sentiment analyses can include use of knowledge based techniques, statistical methods, and/or hybrid approaches. Knowledge-based techniques classify text by affect categories based on the presence of unambiguous affect words such as "happy", "sad", "afraid", and "bored". Some knowledge bases not only list obvious affect words, but also assign arbitrary words a probable "affinity" to particular emotions.

Statistical methods can leverage elements from machine learning such as latent semantic analysis, support vector machines, "bag of words," semantic orientation, and pointwise mutual information. More sophisticated methods can detect the holder of a sentiment (i.e., the person who maintains that affective state) and the target (i.e., the entity about which the affect is felt). To mine the opinion in context and obtain the feature which has been opinionated, the grammatical relationships of words can be used. Grammatical dependency relations are obtained by deep parsing of the text. Hybrid approaches can leverage both machine learning and elements from knowledge representation such as ontologies and semantic networks in order to detect semantics that are expressed in a subtle manner, e.g., through the analysis of concepts that do not explicitly convey relevant information, but which are implicitly linked to other concepts that do explicitly convey relevant information.

Software tools can deploy machine learning, statistics, and natural language processing techniques. Knowledge based systems can make use of publicly available resources, to extract the semantic and affective information associated with natural language concepts. Sentiment analysis can also be performed on visual or tactile content, i.e., images (including video images).

One or more sentiment parameter that can be determined by activation of speech NLP process 111 and/or text NLP process 113 can include e.g. a "fear" sentiment parameter, an "anger" sentiment parameter, a "sadness" sentiment parameter, a "happiness" sentiment parameter, and/or a "disgust" sentiment parameter. In one embodiment, a sentiment parameter can include a score on a scale of 0.00 to 1.00 that indicates the likelihood that the sentiment exists in the message of a message segment. A score of 0.00 can indicate a 0% likelihood that the sentiment exists and the score of 1.00 can indicate a 100% likelihood that a sentiment exists.

Speech NLP process 111 and text NLP process 113 can be run to perform structuring of a message input by a user. In another aspect, speech NLP process 111 and text NLP process 113 can be run to perform structuring of data from one or more additional system 140 for use in performing a fact check process 115. Structured data structured with use of speech NLP process 111 and/or text NLP process 113 can be stored in data repository 118.

Truthfulness determination process 117 can process message data for determining a parameter indicating a truthfulness of a message. A truthfulness parameter of message data can include a truthfulness of a user when inputting a message having the message data, i.e. whether the user inputting the message having the message data was lying or telling the truth when inputting the message. A truthfulness parameter can be conveniently provided by a probability parameter (e.g. one a scale of 0.00 to 1.00) that specifies a probability that a message is truthful.

With further reference to FIG. 1, messaging system 120 can include an associated data repository 122. In another aspect manager system 110 can include an associated data repository 118. Messaging system 120 can include in repository 122 a collection of files, such as for example, HTML files, CSS files, image files, and JavaScript files. Messaging system 120 can support transmission of speech based messages and/or text based message. Messaging system 120 in one embodiment can include a social network website. Messaging system 120 in one embodiment can be an enterprise messaging system provided by an enterprise that provides an on-line service (e.g. product or service retailing, financial services) unrelated to messaging or social networking. Messaging system 120 in one embodiment can be provided by a cellular network mobile phone and text service.

At block 210 method 200 can include obtaining message data input into a messaging system by a user. At block 220 method 200 can include processing the message data to determine a truthfulness parameter of the message data, the truthfulness parameter indicating a truthfulness of the message data. At block 230 method 200 can include associating the truthfulness parameter to the message data.

Figure 3:
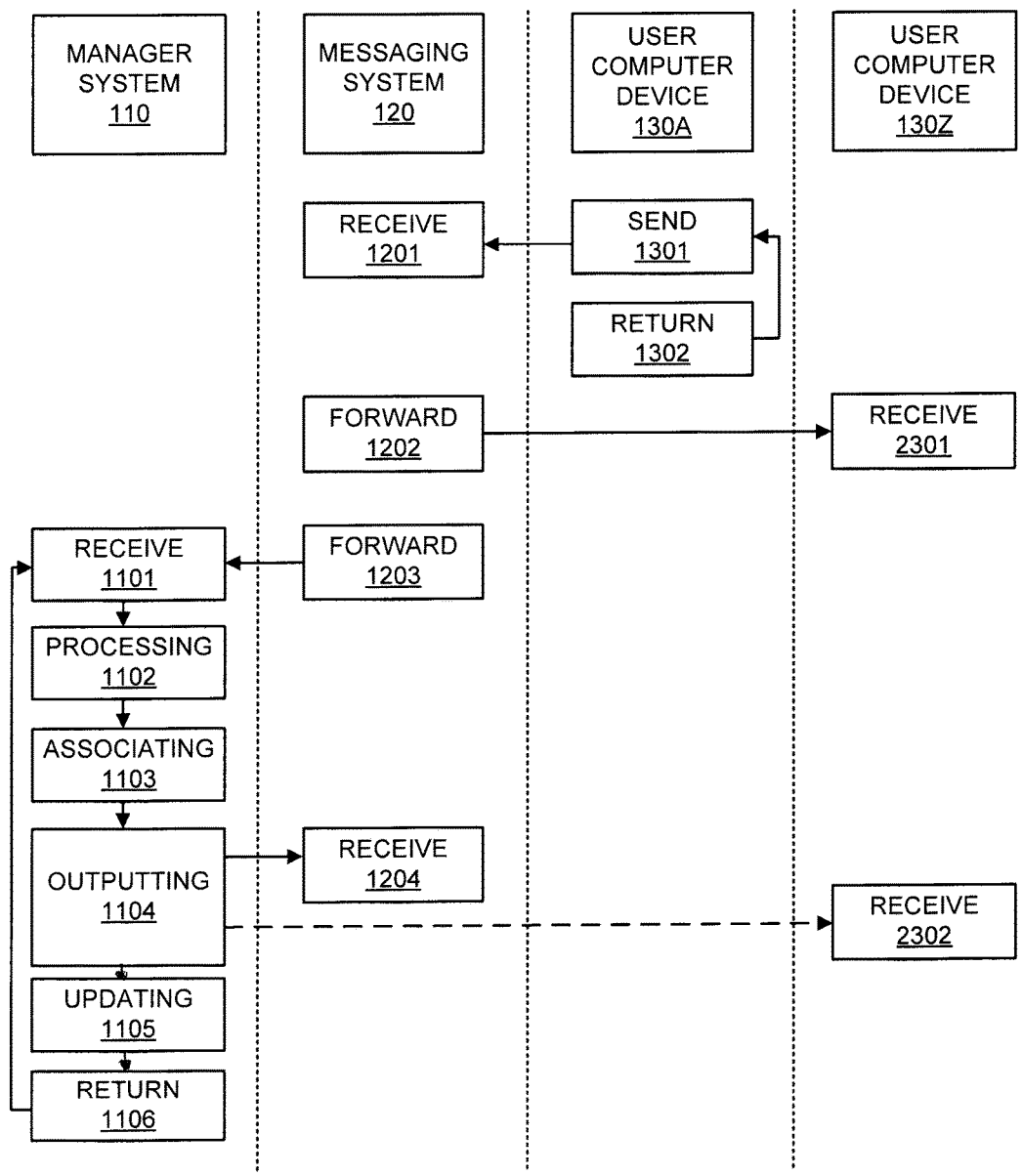
FIG. 3 is a flowchart depicting a method for use in associating a truthfulness parameter to message data in one embodiment.

A flowchart illustrating in one embodiment operation of system 100 is shown in FIG. 3, wherein exemplary functions are described with respect to manager system 110, messaging system 120 and first and second user computer devices 130A and 130Z used by first and second different users. Functions of manager system 110 described in reference to FIG. 5 set forth exemplary functions in accordance with method 200 as set forth in connection with the flowchart of FIG. 4 in one embodiment.

At block 1301 user computer device 130A can send a message to messaging system 120 for reception by messaging system 120 at block 1201. Such message can be a speech based message or text based message. Such message can input by a user of computer device 130A using a user interface of computer device 130A. The user interface can be e.g. an audio input device in the case of the speech based message or a keyboard (e.g. virtual or physical) in the case of a text based message. If the destination of the message sent at block 1301 is another certain user, messaging system 120 can at block 1202 forward the message to the user computer device 130Z of the certain other user for receipt at block 2301. In some embodiments messaging system 120 can be the destination of the message sent at block 1301. At block 1203 messaging system 120 can forward the message sent at block 1301 to manager system 110 for processing. As indicated by return block 1302 user computer device 130A can repeatedly send messages e.g. speech based messages and/or text based messages.

In one embodiment, a message sent at block 1301 and forwarded by messaging system 120 at block 1203 can be accompanied with biometric data associated with a message. The biometric data can include voice data defining a speech based message (where the message is a speech based message) and additional biometric data captured at the time of message input into a computer device, e.g., blood pressure data output from a blood pressure sensor sensing blood pressure of the user of computer device 130A and/or computer device 131A, pulse data output from a pulse sensor sensing a pulse of user of the computer device 130A and/or computer device 130A, a skin conductivity data output from a skin conductivity sensor sensing a skin conductivity of a user of computer device 130A and/or computer device 131A, image data (still and/or video) from a camera of computer device 130A and/or computer device 131A outputting a representative of a user of computer device 130A and/or computer device 131A. There is set forth herein in one embodiment obtaining speech based message data and biometric data of a speaker user of a messaging system, the speech based message data being input into a computer device by the speaker user and the biometric data indicating one or more aspect of a physical condition of the speaker user during the input of the speech based message data into the computer device.

At block 1101 manager system 110 can receive the message sent at block 1301 and at block 1102 can perform processing of data to determine an indicator of truthfulness of message data of the message.

Figure 4:
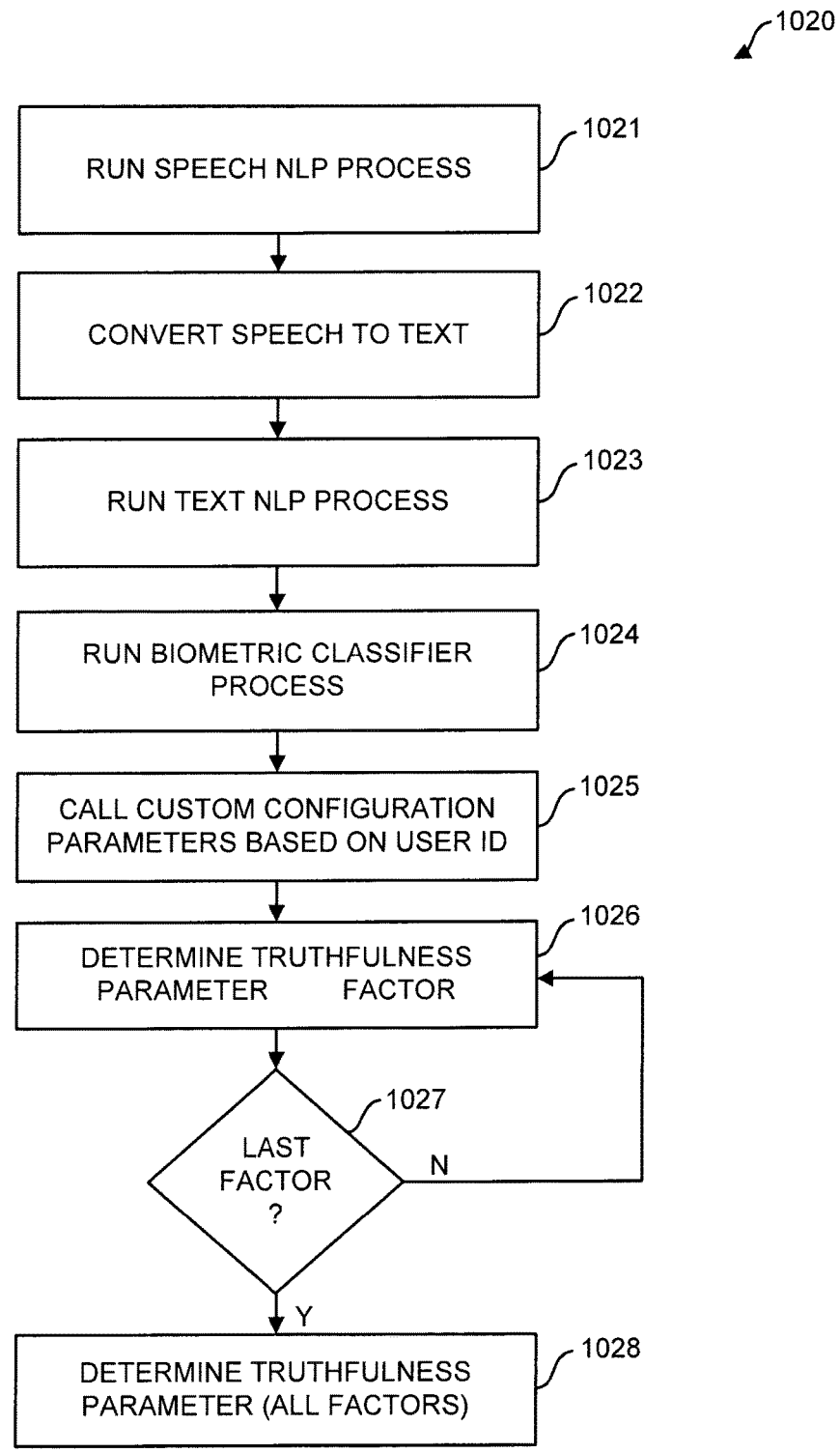
FIG. 4 is a flowchart depicting a method for use in determining a truthfulness parameter to message data in one embodiment.

Manager system 110 in one embodiment for performing processing as set forth at block 1102 can perform the method 1020 as set forth in FIG. 4. At block 1021 manager system 110 can activate speech NLP process 111 to extract sentiment classification from speech, e.g. a "fear" sentiment parameter, an "anger" sentiment parameter, a "sadness" sentiment parameter, a "happiness" sentiment parameter, and/or a "disgust" sentiment parameter. At block 1122 manager system 110 can activate speech to text process 112 to convert speech to text (if originally in speech form). At block 1122 manager system 110 can run text NLP process 113 perform NLP processing of a message to identify classifications for message data of the message e.g. subject matter classification parameter, "financial", "weather", "sports", "politics" "current events" and/or sentiment classifications such as biometric patterns identified in received biometric data. At block 1023 manager system 110 can activate biometric classifier process 114 to classify biometric data into patterns. For example received biometric data provided by image data can be classified into gestures defined by temporal and/or spatial patterns, received biometric data provided by a blood pressure sensor data can be classified into temporal and/or spatial patterns, received biometric data provided by a pulsometer sensor data can be classified into temporal and/or spatial patterns, received biometric data provided by a skin conductivity sensor data can be classified into temporal and/or spatial patterns, and received biometric data provided by breathing data (e.g. provided by activation of speech NLP process) can be classified into temporal and/or spatial patterns. Where speech based message data and biometric data of speech based message data originate from different data streams (one data stream for the message data and another data stream for the biometric data) manager system 110 can examine timestamps of the different data streams so that biometric data subject to processing is appropriately correlated to time periods of message data input.

At block 1025 manager system 110 can call custom configuration parameters from repository 118 for customizing the truthfulness parameter determination based on the current user. At block 1026 manager system 110 can determine a truthfulness parameter for message data according for a truthfulness indicating factor. An administrator can define any number of truthfulness indicating factors. An administrator can work under the advisement of a polygraph expert to implement a preferred polygraph technology out of a plurality of candidate polygraph technologies. A given truthfulness indicating factor can include examination of one or more data outputs. The data outputs can of a single output type or a plurality of output types. Output types can include e.g. a biometric output, a fact check output, and an NLP output.

At block 1027 manager system 110 can determine if there are further truthfulness parameter factors defined for examination in the current truthfulness determination. If there are further factors defined, manager system 110 can return to block 1026 to complete determination of a truthfulness parameter. If there are no further truthfulness factors defined manager system 110 can proceed to block 1028 to complete a truthfulness determination for message data based on the one or more factor subject to determination at block 1028.

A truthfulness parameter determination can be based on one or more defined truthfulness parameter factor and can be given generally by the formulas.

$$P(\text{truthfulness}) = W1PF1 \tag{Eq. 1}$$

$$P(\text{truthfulness}) = W1PF1 + W2PF2 \tag{Eq. 2}$$

$$P(\text{truthfulness}) = W1PF1 + \ldots W(N-1)PF(N-1) + WN\text{-}PFN \tag{Eq. 3}$$

Eq. 1 is an exemplary formula for use by manager system 110 at block 1028 determining truthfulness in the case one truthfulness factor is defined. Eq. 2 is an exemplary formula for use by manager system 110 at block 1028 determining truthfulness in the case two truthfulness factors are defined. Eq. 3 is an exemplary formula for use by manager system 110 at block 1028 determining truthfulness in the case three of more truthfulness factors are defined. In the above equations P indicates a truthfulness parameter of message data of a message, W indicates weight of a given factor and PF indicates the determined truthfulness parameter for a given factor which can be determined by manager system 110 at block 1026. The values of a truthfulness parameter can be expressed in any units and in one embodiment are expressed as a scoring value. In one embodiment, a truthfulness parameter can be scaled normalized and expressed as a probability of being knowingly truthful with a value of 1.00 indicating a 100% probability of being knowingly truthful and a value of 0.00 indicating a 0% probability of being knowingly truthful. A truthfulness parameter can be regarded to be an untruthfulness parameter. For example in one embodiment, a truthfulness parameter indicting a 10 percent probability of message data being knowingly truthful (that the speaker or writer of the speech or text based message data told the truth) indicates a 90 percent probability of the message data being knowingly untruthful (that the speaker or writer lied).

It will be recognized that operations of manager system 110 can vary depending on the number of truthfulness factors defined and the characteristics of the various factors that are defined. Various factors that can be defined e.g. by an administrator and/or a user are summarized in Table A.

TABLE B

| FACTOR | NLP | BIOMETRIC | FACT CHECK | WEIGHT |
|---|---|---|---|---|
| F1 | — | Blood Pressure | — | 0.15 |
| F2 | — | Pulse | — | 0.10 |
| F3 | — | Skin Conductivity | — | 0.15 |
| F4 | — | Breathing | — | 0.10 |
| F5 | — | Gesture | — | 0.10 |
| F6 | — | — | Correctness (lower overhead) | 0.20 |
| F7 | — | — | Correctness (higher overhead) | 0.20 |

According to factor F1, manager system 110 can determine a truthfulness factor parameter by performance of processing that includes examining biometric data provided by blood pressure data of the user initiating the current message received at block 1101. For example, manager system 110 can examine an emotional range parameter.

According to factor F2, manager system 110 can determine a truthfulness factor parameter by performance of processing that includes examining biometric data provided by pulse data of the user initiating the current message received at block 1101.

According to factor F3, manager system 110 can determine a truthfulness factor parameter by performance of processing that includes examining biometric data provided by skin conductivity data of the user initiating the current message received at block 1101.

According to factor F4, manager system 110 can determine a truthfulness factor parameter by performance of processing including examining biometric data provided by breathing biometric data of the user initiating the current message received at block 1101. On one embodiment breathing data can be extracted from voice data as part of performance of speech NLP process at block 1021.

According to factor F5, manager system 110 can determine a truthfulness factor parameter by performance of processing including examining biometric data provided by gesture data, gesture data can be provided by processing of image data representative of a user and/or motion data of a user. Gesture data can include e.g. having gestures, body gestures, facial gestures (i.e. facial expressions).

According to factor F6, manager system 110 can determine a truthfulness parameter by performance of processing including examining of an output of a fact check process 115. If facts of a message are consistent with a source compared to (a past statement by the current user or another user, a statement in a reporting of a past historical event, a statement in a reporting of a live event) truthfulness can be specified to be indicated (e.g. with an increased truthfulness parameter value) whereas if facts of a message are inconsistent with facts of a source compared to untruthfulness can be specified to be indicated (e.g. with a decreased truthfulness parameter value). In one aspect, manager system 110 can perform a fact check by comparing content of a current message of current user to content of a past message of the current user or other user of system 100 stored in message history area 1181 of data repository 118. In one aspect manager system 110 can perform a fact check by comparing content of the current message to content of one or more additional system 140, such a public database of one or more additional system 140 storing reports of facts or in the case a current topic is a current event a live data stream feed of the current event.

According to factor F7, manager system 110 as with factor F6 can determine a truthfulness parameter by performance of processing including examining of an output of a fact check process 115. In one embodiment, as illustrated in Table A, fact check factor F7 can be differentiated from factor F6 by involving a relatively higher overhead fact check process whereas factor F6 can involve a relatively lower overhead fact check process. A relatively higher overhead process can feature greater processing resource consumption than a relatively low overhead process. In one embodiment, determining a truthfulness parameter factor according to factor F6 can include using data of internal data repository 118 and can be absent of communications with an external additional system 140 whereas determining a truthfulness parameter factor according to factor F7 can include communications, e.g. database data acquisitions receipt of live data streams with an external additional system 140. System 100 can be configured to support "real time" operation characterized by an absence of a substantial user perceivable delay between a time of message input into a user computer device e.g. computer device 130A indicated at block 1301 and a control implementation (e.g. a perceivable alert indicated by block 2302 or access to an electronic asset indicated by block 1204).

Manager system 110 can use an output of the Text NLP process 113 for performance of a fact check process. Speech NLP process 111 and text NLP process 113 can be run to perform structuring of a message input by a user. In another aspect, speech NLP process 111 and text NLP process 113 can be run to perform structuring of data from one or more additional system 140 for use in performing a fact check process 115. Structured data structured with use of speech NLP process 111 and/or text NLP process 113 can be stored in data repository 118.

Associating at block 1103 can include tagging a message with one or more truthfulness parameter according to a process described and with one or more NLP process output that can be output at block 1021 including one or more sentiment parameter so that at block 1103 a message can be provided that is tagged with both one or more sentiment parameter and one or more truthfulness parameter.

In the examples of Table A, a blank in a cell can indicate that the output type is not examined during a determination according to the indicated truthfulness parameter factor. In one embodiment, a user interface can be presented e.g. for presentment on a computing node of manager system 110 which allows an administrator user to define new factors to be determined and/or to cancel factors and/or to change weights associated with factors. Such a user interface can alternatively or additionally be presented to a user at one or more of user computer devices 130A-130Z.

On completion of processing for determining a truthfulness parameter at block 1102 manager system 110 can proceed to block 1103 (FIG. 3) to perform associating of the truthfulness parameter to the message data. In one embodiment, associating at block 1103 can include tagging of text associated to message. Tagging can include reformatting of an input speech or text based message to include one or more tag defined in a header or footer or message data of a message specifying the determined truthfulness parameter. Tagging in one embodiment can include providing original content of a message and/or references to the content and one or more truthfulness parameter in a common marked up language document. Associating at block 1103 can include tagging message data with one or more truthfulness parameter according to a process described and with one or more NLP process output that can be output at block 1021 and/or block 1023 including one or more sentiment parameter so that at block 1103 a message can be provided that is tagged with both one or more sentiment parameter and one or more truthfulness parameter.

At block 1104 manager system 110 can perform outputting of a communication based on a result of the processing. In one embodiment, a communication output by manager system 110 can be a communication to initiate access or denial of access to an electronic asset. For example manager system 110 can assign different security privilege levels to different users, the privilege levels determining access to different electronic assets. At block 1102 manager system 110 can perform processing and determine that a message is untruthful and responsively can perform outputting at block 1104 of a communication for receipt by messaging system 120 at block 1204 to decrease a privilege level of the user inputting the message subject to processing at block 1102, to remove access to certain electronic assets. Thus, system 100 provides a computer security feature to reduce privileges of users regarding digital rights and to restrict access to electronic asserts.

In another embodiment of manager system 110 at block 1104 performing outputting of communication based on a result of the processing, manager system 110 can send an alert to a user. For example a first user at first computer device 130A can be engaged with a speech based teleconference with a second user at computer device 130Z and may be inputting speech based messages into computer device 130A. Responsively to processing at block 1102 indicating that a message data of a current message is untruthful, manager system 110 at block 1104 can output a communication received by the computer device 130Z to initiate an alert (e.g. audio and/or video based) perceivable by the user of computer device 130Z warning of the untruthful message data. Untruthfulness can be determined on the basis of a value of a truthfulness parameter being below a threshold.

Truthfulness parameter determinations as set forth herein can be used in other applicants. In addition to controlling access to electronic assets, determined truthfulness parameters can be used to automatically control access to physical assets such as use of machinery e.g. vehicles requiring a requisite level of access or access to physical spaces such as locations of a workspace.

At block 1105 manager system 110 can perform updating of data of data repository 118 data for the user inputting the current message. For example, the current message can be stored in raw form and/or in structured form as history messages of message history area 1181 and biometric data for the current message received at block 1101 can further be stored. In one embodiment, updating at block 1105 can perform activating a machine learning process 116 so that a procedure for performing processing at block 1105 is recalibrated based on the current message. In one embodiment, manager system 110 for performance of machine learning can examine behavior data of past messages (indicating behavior of the speaker or writer of the speech or text based message during message input) having low truthfulness values according to a truthfulness determination process (e.g. determining of a truthfulness parameter and/or one or more truthfulness parameter factor) in search of behavior patterns defined by biometric data and/or NLP output data that is commonly present when there is message with a low truthfulness parameter. In one embodiment a single truthfulness parameter factor can be used for such determination, namely the factor of whether the message data is or is not factually correct (factor F6 of Table A). As indicated by return block 1106 manager system 110 can repeatedly perform blocks 1101-1105 on an open loop basis.

In one embodiment, manager system 110 can track behavior patterns of a user during input of a speech or text based message for each message determined to be untruthful (e.g. yielding a truthfulness value below a threshold). On receipt of a threshold number of samples manager system 120 for performance of a machine learning process 116 can identify behavior patterns commonly exhibited by the speaker or writer when an untruthful speech or text based message is input as signature behavior patterns indicative of untruthfulness which can be registered in data repository 118 as signature behavior patterns 1182. In one embodiment manager system 110 can identify a behavior pattern as a signature biometric pattern if more than J % of messages having a truthfulness value of less than K have associated therewith the behavior pattern. A behavior pattern can be a biometric pattern e.g. a blood pressure pattern, a pulse pattern, a skin conductivity pattern, a breathing pattern (e.g. output by activation of speech NLP process 111), a gesture, or a combination of such patterns. Patterns can be temporal and/or spatial. A behavior pattern can alternatively or in addition to be defined by an NLP output pattern, e.g. a specific combination of sentiment parameters and/or topic classification of a message (e.g. it can be determined that a user commonly is angry and sad (or other combination of one or more sentiment) when lying, or commonly talks about Texas (or other topic subject to classification) when lying.

Manager system 110 in performing updating at block 1105 can update a process for determining a truthfulness parameter of message data. In one embodiment, where a pattern identified and registered as a signature behavior pattern corresponds to a pattern already being subject to examination according to a currently defined truthfulness parameter factor such as a factor explained in reference to Table A and affects a value of a truthfulness parameter factor, manager system 110 can automatically adjust the weight for the factor and can automatically adjust weights for other factors. In one embodiment, where a pattern identified as a signature behavior pattern does not correspond to a pattern already being subject to examination according to a currently defined truthfulness parameter factor such as a factor explained in reference to Table A, manager system 110 can automatically define a new factor for examination and a weight for the new factor and can adjust weights of other factors. In one example, on the identification and registration of a new certain signature behavior pattern not currently subject to examination by a currently defined factor a new factor "factor F8" can be automatically established causing manager system 110 to examine for the presence of the certain signature behavior pattern that has been registered into data repository 118 responsively to receipt of a next message from the current user. Based on the signature behavior pattern detected, the new factor "factor F8" automatically established can be defined so that manager system 110 examines a combination of one or more NLP output parameter, and/or one or more biometric output parameter for determination of the new truthfulness parameter factor.

There is set forth herein a system 100 featuring image analysis processing of user image representations and/or or other biometrics (possibly a smartwatch) in order to determine from visual clues or other biometrics the probability of truth behind a user's statements made in messages. Comparisons against known truths from e.g. the news or past statements can be used in certain embodiments. By implementation of machine learning process 116 self-learning capabilities to learn behaviors e.g. habits and fidgets of people while knowingly providing falsehoods can be provided.

There is set forth herein in one embodiment a probability analysis on whether the words (speech or text) represent a falsehood knowingly presented. Such probability analysis can be applied the spoken word more than the written word. An analysis in one embodiment can be based on image analysis processing and/or other biometric data processing (possibly provided by a smartwatch) in order to figure out from visual clues or other biometrics the probability of truth behind those statements. That is the additional capability and it fits in nicely with what is already done in the world of emotional tagging. By implementation of machine learning process 116 self-learning aspects such that e.g. gestures of an individual or other behavior pattern can become known over time. Individuals may have certain behaviors that can be learned by the system pertaining to falsehoods knowingly presented.

In one embodiment a speech segment can be tagged with metadata. If tagging is performed properly, then emotion (which can be indicated by one or more sentiment parameter) to text correlation can be provided. There is set forth herein a process for initial tagging of emotion (which can be indicated by one or more sentiment parameter) to text snippets (words, phrases, sentences, paragraphs, etc.). There is set forth herein extending initial tagging of emotion and providing a probability analysis on whether the words (speech or text) represent a falsehood knowingly presented. The probability analysis can be applied to the spoken word or the written word. There is set forth herein an analysis based on image analysis processing and/or other biometrics (e.g. with use of a mobile device and/or a smartwatch) in order to figure out from visual clues or biometrics the probability of truthfulness behind those statement. There is set forth herein performing speech to text where there is performed NLP processing on text to determine emotion and tag it to segments of sentences. Having tagged emotions would have an accuracy increase in the text to speech phase, so long as the tagging is accurate. There is set forth herein extending the part of emotion tagging and providing a probability analysis on whether the words (speech or text) represent a knowingly presented falsehood. There is set forth herein improved accuracy of having tagged words or sentences to emotion indicated by sentiment parameters. There is set forth herein extending that part and providing a probability analysis on whether the words (speech or text) represent a falsehood knowingly presented.

A method set forth herein can include providing a probability analysis on whether the words (speech or text) represent a knowingly presented falsehood. One or more truthfulness parameter can be tagged to an input message alone on in combination with one or more parameter of one or more other type determined by activation of speech NLP process 111 and/or text NLP process 113.

By activation of a truthfulness determination process 117 a determination of the probability of lying can provide a truthfulness parameter which parameter can be tagged to a message of the user. In one embodiment, while a speaker provides a long speech sample having most content determined to be truthful a small segment of the sample, e.g. "tried to hire Jeff but failed" can be determined to untruthful (having a truthfulness parameter value less than a threshold) and can be tagged with 82 percent probability of lying (18 percent likelihood of being truthful) based on the clues picked up by the system. The clues can include (a) image analysis (which can include video analysis) such that certain known gestures can be picked up on (e.g. typically users look away while lying, blink in certain ways, or fidget in a certain way), and (b) other biometrics. In one embodiment, a truthfulness determination process 117 can include activation of a fact check process 115. A fact check process can include a comparison of facts of a current message to facts of past statements on the spoken topic e.g. past statements of the user, past statements of other users of system 100, past statements by members of the public (e.g. the press) as can be determined from data streams obtained from one or more additional system 140 external to manager system 110.

Components of system 100 can include in one embodiment (a) biometric analysis provided by mage analysis. In some embodiments, image analysis can be used in real time determine if a person may be lying. Various indicators can include detection of gestures e.g. rolling of the eyes upward, or blinking or looking away, etc. In some embodiments images subject to processing can images captured by associated computer device 131A provided by a user who is using a computer device 130A provided by a smartphone to make a voice phone call in which speech based messages are input into computer device 130A. Components of system 100 can include in one embodiment (b) other biometrics. In some embodiments, biometrics other than image analysis may be used to pick up additional clues. For example, heart rate data as provided by a pulsometer can be examined, as well as biometric data such as blood pressure sensed using a blood pressure sensor, skin conductivity data as sensed by a skin conductivity sensor and breathing data which can be discerned by activation of speech NLP process 111. System 100 can be customized to operate according to different polygraph technologies. In one embodiment biometric sensors such as pulsometers, blood pressure sensors, and skin conductivity sensors can be disposed in a computer device 131A provided by a smartwatch which can remain in proximity with a body of a user throughout its use. Components of system 100 can include in one embodiment (c) data streaming from various news sites. In some embodiments, a fact check process 115 can be employed real time comparison of certain statements can be made against past statements made or against news stories. This technique may be used as evidence when the other clues are indicative of possible lying. Components of system 100 can include in one embodiment (d) Natural Language Processing (NLP). NLP classification techniques can be used to break down important aspects of the data streams as they are read in to our system. Components of system 100 can include in one embodiment (e) a knowledge base provided by data repository 118 can be used to remember the behaviors that specific individuals have when not telling the truth. If a certain user has been determined to knowingly provide false information 5 previous times based on other clues, the system may notice that in all 5 cases, the person scratches his left arm with his right arm while he is speaking those falsehoods knowingly presented. Now the system has determined that this particular gesture is indicative of lying going forward. Components of system 100 can include in one embodiment (f) the knowledge base provided by data repository 118 also storing addition information such as data collected in the data streaming process for performance of a fact check.

Figure 2:
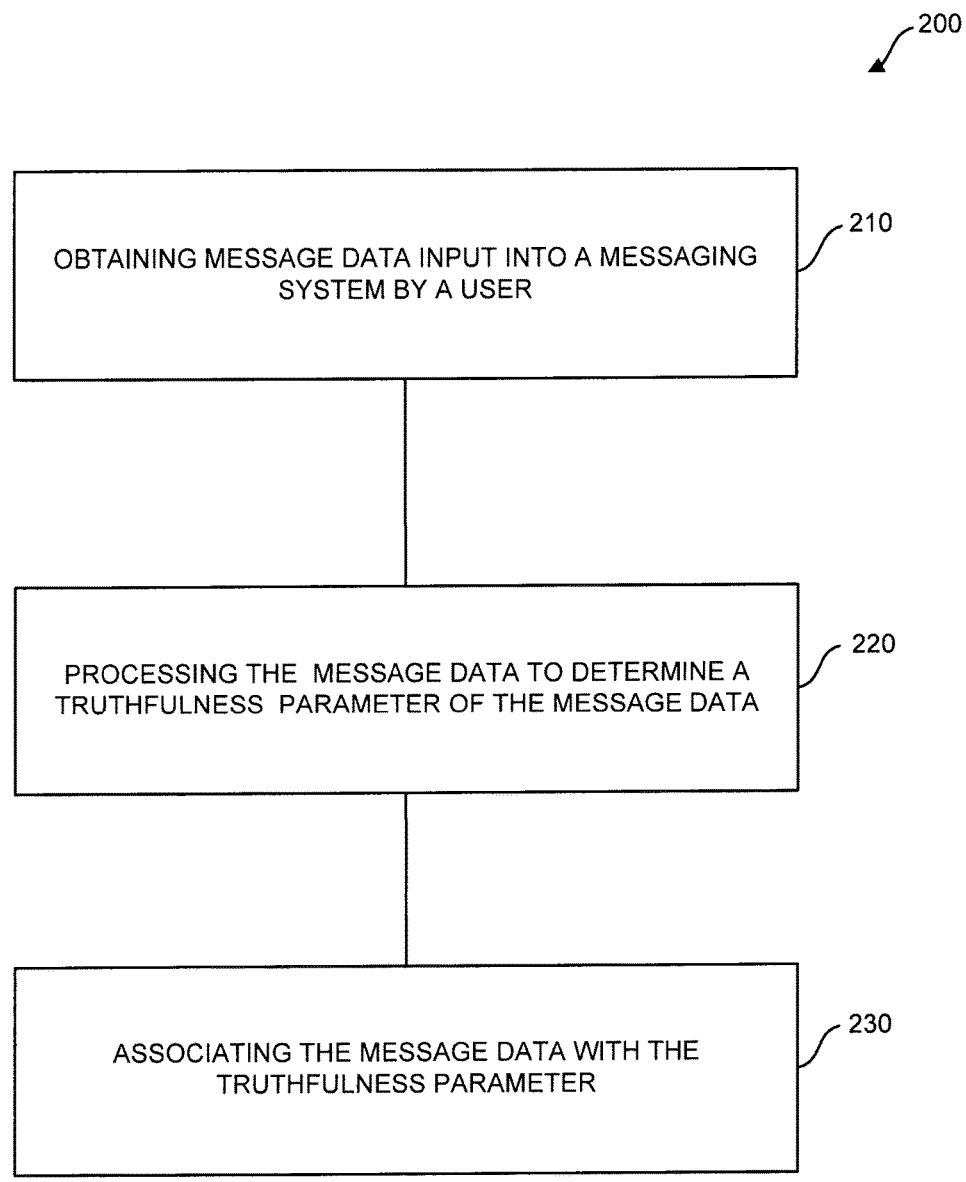
FIG. 2 is a flowchart illustrating method for use in associating a truthfulness parameter to message data in one embodiment.

According to method 200 as set forth in the flowchart of FIG. 2 a speech NLP process 111 and a text NLP process 113 can be run to automatically determine sentiment parameters for received message data. Sentiment can be determined e.g. based on language used (certain word patterns are known to correlate to certain emotions) volume of voice (in the case of speech) punctuation (in the case of written text)

Sentiments can be determined for messages, e.g. speech based messages or text based messages or parts of a message. According to one embodiment sentiment can be determined and tagged for any phrase or any word or any sentence. In one example an incoming message can be: "I can't believe the team made it to the championship". When one user says it, they are mad, because their team did not make it and maybe the person thought their team was better and the team in the championship got lucky. Clues such as intonation and the delivery of the sentence can pick up on that, e.g. by activation of speech NLP process 111. When another user delivers the speech based message with a different intonations, they are relieved/happy, and that would be tagged to the phrase when they said it. The sentiment parameters can then be tagged to that snippet of words so that the sentiment indicative of emotion is not lost for future readings or text to speech.

As set forth herein there is provided a method for probabilistic analysis for predicting when a speaker or writer is lying and tagging that information accordingly, so that it is also not lost. In one embodiment a receiving message can be subject to processing and tagged with one or more sentiment parameter as well as one or more truthfulness parameter.

In one example a user speech based message with most of the content determined and tagged to have a low probability of lying but having the small phrase "tried to hire Jeff, but it just did not work out" tagged with 82 percent probability of lying (18 percent probability of telling the truth) based on the clues picked up by the system 100 by activation of truthfulness determination process 117. These clues can be based on: Image analysis, other biometrics, activation of a fact check process 115 for comparison of a statement of a message e.g. to other stories in the news or in social sites or as spoken by others. In one embodiment, data streams from news and social media system using speech NLP process 111 and/or text NLP process 113 to collect specific information and storing that information in a knowledge base provided by data repository 118. Data stream comparison can involve comparing small snippets obtained from external additional system 140 external to manager system 110 against data of data repository 118 containing previously collected information from the data streams. Data stream analysis using data from a system external from manager system 112 can be significantly resource consuming and according in one embodiment system 100 can be operative to conditionally perform data stream analysis.

System 100 can be operative learn over time the habits of users when they lie by activation of machine learning process 116. For example, if a user has been determined to have knowingly provided false information 5 previous times based on other clues, the system 100 may determine that in all 5 cases, the user exhibits a behavior including the gesture of scratching his left arm with his right arm while he is speaking those falsehoods knowingly presented. System 100 can identify and register such behavior pattern as a signature behavior pattern. Now the system 100 has determined that this particular gesture is indicative of lying going forward.

Certain embodiments herein may offer various technical computing advantages, involving computing advantages to address problems arising in the realm of computer networks such as improved processing of user initiated communications by improvement data structuring of user initiated messages. In one embodiment, data structuring as set forth herein can be used in security applications to establish privileges and to grant or deny access to electronic assets. Data structuring as set forth herein can be used in machine control applications and to establish alerts. By providing addition information about a user using a computer network embodiments herein can reduce or eliminate critical processing and data acquisition delays in a variety of emergency situations (e.g. health or business) involving online computer network environments. Embodiments herein can employ data structuring processes, e.g. involving use of data outputs from biometric sensors, NLP processes and other classifiers. Embodiments herein can provide results and advantages that are not possible or practical without use of components of a technical computing environment, such as automatic tagging of voice samples and/or text samples with classifiers that specify truthfulness parameters having truthfulness parameter values. In some embodiments a machine learning process can be employed so that determination of truthfulness can benefit based on exhibited behavior of a user.

Figure 5:
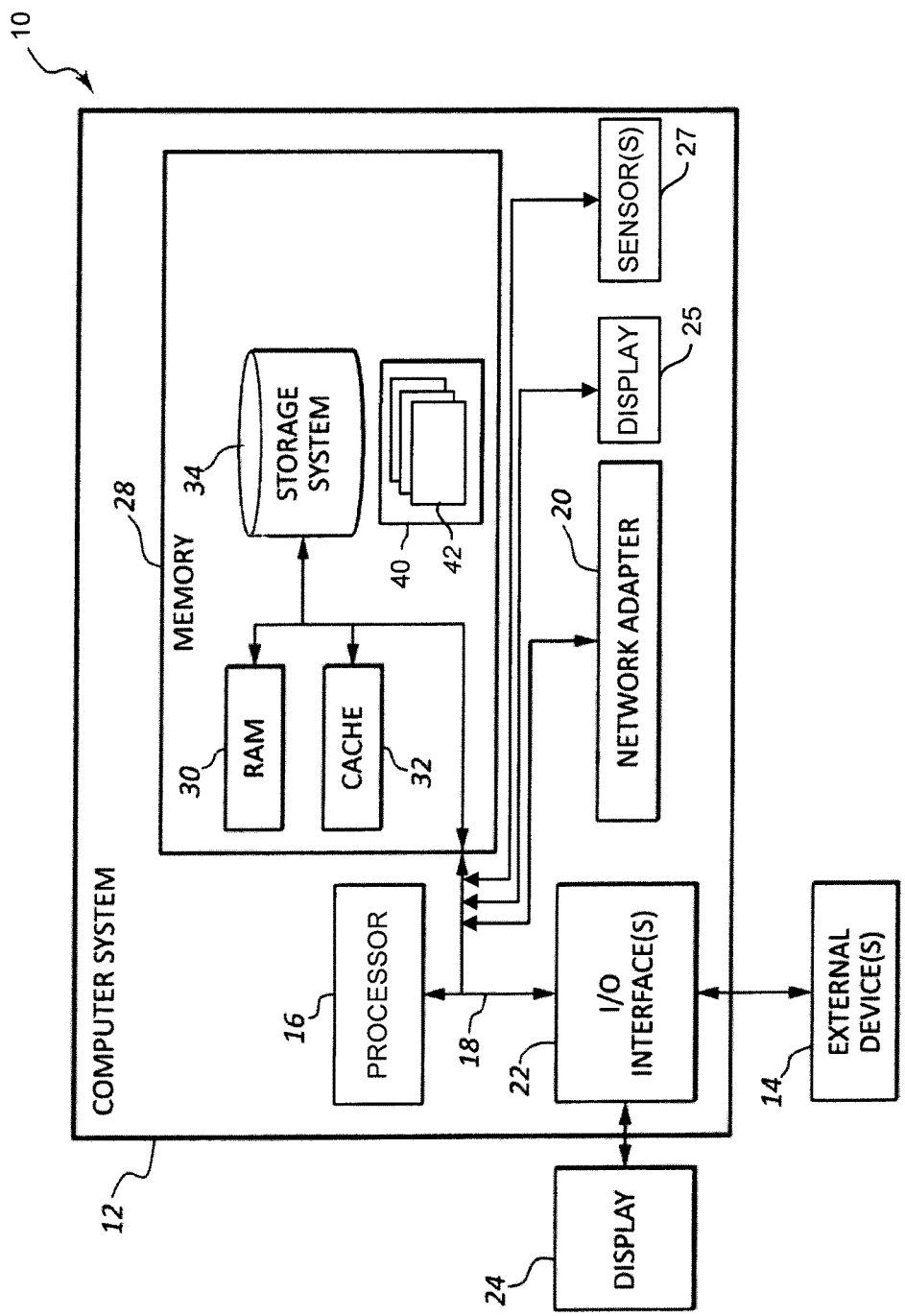
FIG. 5 depicts a computing node according to one embodiment.
Figure 6:
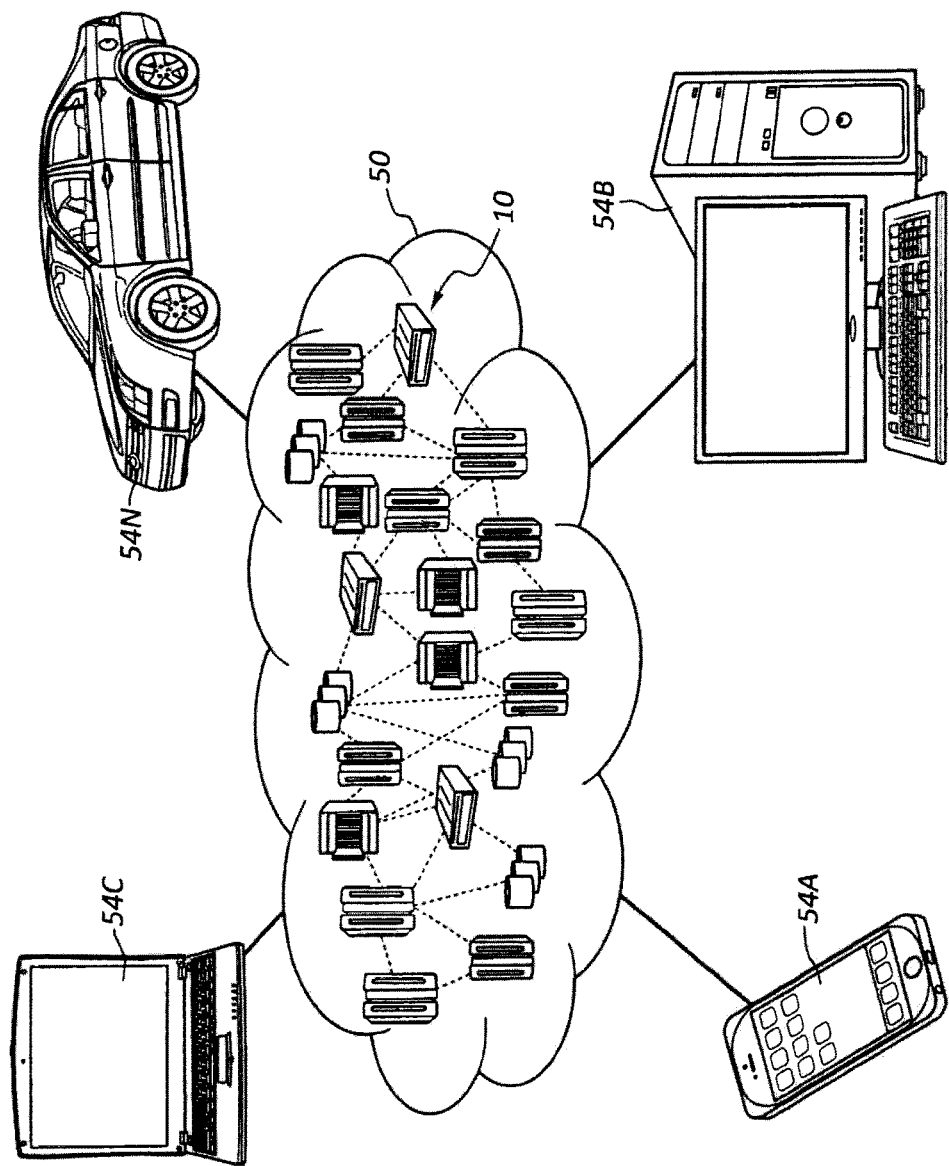
FIG. 6 depicts a cloud computing environment according to one embodiment.
Figure 7:
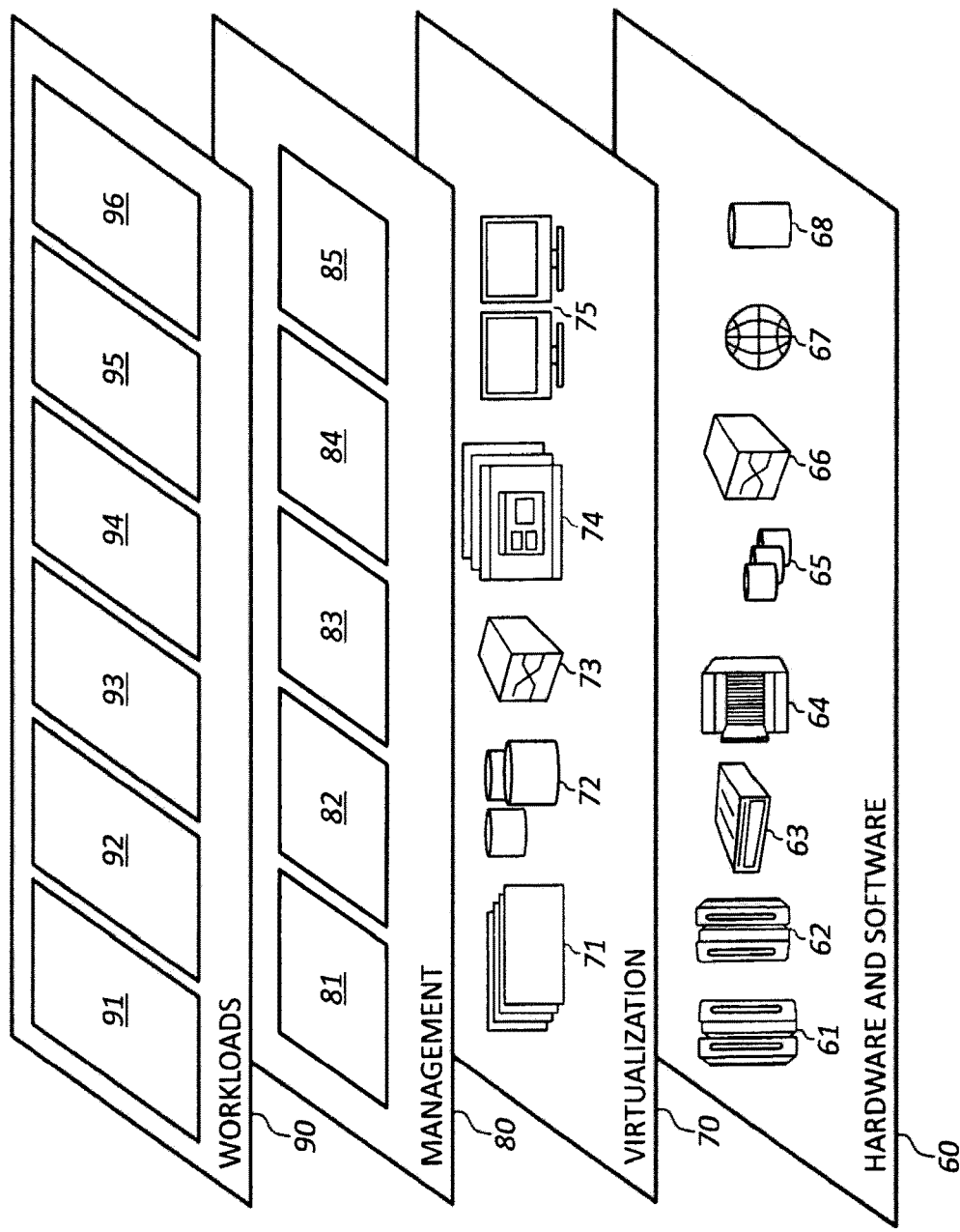
FIG. 7 depicts abstraction model layers according to one embodiment.

FIGS. 5-7 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 5, a schematic of an example of a computing node is shown. Computing node 10 is only one example of a computing node suitable for use as a cloud computing node and is not intended to suggest any limitation as to the scope of use or functionality of embodiments of the invention described herein. Regardless, computing node 10 is capable of being implemented and/or performing any of the functionality set forth hereinabove. Computing node 10 can be implemented as a cloud computing node in a cloud computing environment, or can be implemented as a computing node in a computing environment other than a cloud computing environment.

In computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 5, computer system 12 in computing node 10 is shown in the form of a computing device. The components of computer system 12 may include, but are not limited to, one or more processor 16, a system memory 28, and a bus 18 that couples various system components including system memory 28 to processor 16. In one embodiment, computing node 10 is a computing node of a non-cloud computing environment. In one embodiment, computing node 10 is a computing node of a cloud computing environment as set forth herein in connection with FIGS. 6-7.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. One or more program 40 including program processes 42 can generally carry out the functions set forth herein. In one embodiment, manager system 110 can include one or more computing node 10 and can include one or more program 40 for performing functions described with reference to method 200 of FIG. 2, and the functions described with reference to manager system 110 as set forth in the flowchart of FIG. 3 and the flowchart of FIG. 4. In one embodiment, messaging system 120 can include one or more computing node 10 and can include one or more program 40 for performing functions described with reference to messaging system 120 as set forth in the flowchart of FIG. 3. In one embodiment, one or more user computer device 130A-130Z can include one or more computing node 10 and can include one or more program 40 for performing functions described with reference to one or more user computer device 130A-130Z as set forth in the flowchart of FIG. 3.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples include, but are not limited to: microcode, device drivers, redundant processing units, external disk drive arrays, RAID systems, tape drives, and data archival storage systems, etc. In addition to or in place of having external devices 14 and display 24, which can be configured to provide user interface functionality, computing node 10 in one embodiment can include display 25 connected to bus 18. In one embodiment, display 25 can be configured as a touch screen display and can be configured to provide user interface functionality, e.g. can facilitate virtual keyboard functionality and input of total data. Computer system 12 can include one or more network adapter 20.

Computer system 12 in one embodiment can also include one or more sensor 27 connected to bus 18. One or more sensor 27 can alternatively be connected through I/O interface(s) 22. One or more sensor 27 can include a Global Positioning Sensor (GPS) device in one embodiment and can be configured to provide a location of computing node 10. In one embodiment, one or more sensor 27 can alternatively or in addition include, e.g., one or more blood pressure (bp) sensor, one or more pulsometer, one or more skin conductivity sensor, or one or more audio input device one or more of a camera, one or more gyroscope, one or more temperature sensor, one or more humidity sensor. As noted, in some embodiments a user can use a plurality of computer device, e.g. can use a computer device 130A and an associated computer device 131A. In one embodiment computer device 130A can be provided e.g. by a smartphone and associated computer device 130A can be provided by a smartwatch that is configured to automatically upload sensor data to computer device 130A which data can be uploaded to manager system 110. In such an embodiment, the noted types of one or more sensor 27 can be duplicated between the associated computer devices e.g. computer devices 130A and 131A or distributed between the computer devices so that some of the one or more sensors are in one of the computer devices 130A or 130Z and other of the one or more sensor 27 are in the remaining computer device 130A or 130Z. It can be advantageous to dispose certain types of biometric sensors in a smartwatch, e.g. a pulsometer, skin conductivity sensor, in view of the persistent position of a smartwatch in proximity with a user's body. In FIG. 6 computing node 10 is described as being implemented in a cloud computing environment and accordingly is referred to as a cloud computing node in the context of FIG. 6.

Referring now to FIG. 6, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Referring now to FIG. 7, a set of functional abstraction layers provided by cloud computing environment 50 (FIG. 6) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components 96 for truthfulness determining and associating as described herein. The processing components 96 can be implemented with use of one or more program 40 described in FIG. 5.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Forms of the term "based on" herein encompass relationships where an element is partially based on as well as relationships where an element is entirely based on. Methods, products and systems described as having a certain number of elements can be practiced with less than or greater than the certain number of elements. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A method comprising:
   obtaining speech based message data and biometric data of a speaker user of a messaging system, the speech based message data being input into a computer device by the speaker user and the biometric data indicating one or more aspect of a physical condition of the speaker user during the input of the speech based message data into the computer device;
   processing data to determine a truthfulness parameter of the speech based message data, the processing data to determine a truthfulness parameter including processing the biometric data, the truthfulness parameter indicating a probability that the speech based message data is knowingly untruthful; and
   associating the truthfulness parameter to the speech based message data, wherein the associating includes tagging the speech based message data with the truthfulness parameter, wherein the processing includes performing a preliminary truthfulness determining process, the preliminary truthfulness determining process based on examining of biometric data, and wherein the processing includes performing a fact check process to determine factual correctness of content of the message data conditionally on the condition that the preliminary truthfulness determining process satisfies a criteria.

2. The method of claim 1, wherein the method includes activating a speech Natural Language Processing (NLP) process to determine a sentiment parameter of the speech based message data, and wherein the method includes tagging the speech based message data with the sentiment parameter.

3. The method of claim 1, wherein the processing includes determining the truthfulness parameter based on one or more of the following selected from the group consisting of: (a) a fact check process output, wherein the fact check process checks factual correctness of statements of the speech based message data, and (c) an NLP process output, wherein the NLP process is performed using the speech based message data.

4. The method of claim 1, wherein the processing includes determining the truthfulness parameter based on each of (a) a fact check process output, wherein the fact check process checks factual correctness of statements of the speech based message data, and (c) an NLP process output, wherein the NLP process is performed using the speech based message data.

5. The method of claim 1, wherein the biometric data includes one or more of the following selected from the group consisting of (a) received image data, (b) received blood pressure data, (d) received pulse data, (e) received skin conductivity data, and (f) received breathing data.

6. The method of claim 1, wherein the processing includes determining the truthfulness parameter based on received biometric data provided by breathing data, the breathing data being provided by activating a speech NLP process to process the speech based message data.

7. The method of claim 1, wherein the method includes responsively to the processing initiating one or more of the following selected from the group consisting of: (a) a change in digital rights defining access to a security protected electronic asset, (b) an alert, and (c) a change in access to a physical asset.

8. The method of claim 1, wherein the processing includes performing a preliminary truthfulness determining process, the preliminary truthfulness determining process based on examining of biometric data and on an output of a first fact check process, and wherein the processing includes performing a second fact check process to determine factual correctness of content of the message data conditionally on the condition that the preliminary truthfulness determining process satisfies a criteria, the second fact check process consuming processing resources in excess of processing resources consumed by the first fact check process.

9. The method of claim 1, wherein the method includes performing a machine learning process for identifying signature behavior patterns for the user, the signature behavior patterns identified by the performing a machine learning process including signature biometric patterns identified as being exhibited by the user on input of message data that satisfies a criteria, and wherein the processing includes examining the biometric data for the speech based message data to determine whether a signature biometric pattern of the signature biometric patterns is included in the biometric data.

10. The method of claim 1, wherein the method includes performing a machine learning process for identifying signature behavior patterns for the user, the signature behavior patterns identified by the performing a machine learning process including signature behavior patterns identified as being exhibited by the user on input of message data that satisfies a criteria, and wherein the processing includes examining NLP output data for the speech based message data to determine whether a signature NLP pattern of the signature NLP patterns is included in the NLP output data.

11. The method of claim 1, wherein the processing includes performing processing based on user defined configuration data entered into a user interface, the user interface including on or more of the following selected from the group consisting of (a) a user interface for use by an administrator user, and (b) a user interface for use by a user of a messaging system.

12. The method of claim 1, wherein the method includes converting speech of the speech based message data into text, activating a text based Natural Language Processing (NLP) process to determine a sentiment parameter of the speech based message data, and wherein the method includes tagging the speech based message data with the sentiment parameter, wherein the processing includes determining the truthfulness parameter based on received biometric data for the message data, the received biometric data provided by one or more of the following selected form the group consisting of (a) received image data, (b) received blood pressure data, (d) received pulse data, (e) received skin conductivity data, and (f) received breathing data, wherein the processing includes performing a preliminary truthfulness determining process, the preliminary truthfulness determining process based on examining of biometric data, and wherein the processing includes performing a fact check process to determine factual correctness of content of the message data conditionally on the condition that the preliminary truthfulness determining process satisfies a criteria, wherein the method includes responsively to the processing initiating one or more of the following selected from the group consisting of: (i) a change in digital rights defining access to a security protected electronic asset, (ii) an alert, and (iii) a change in access to a physical asset, and wherein the processing includes performing processing based on user defined configuration data entered into a user interface, the user interface including on or more of the following selected from the group consisting of (A) a user interface for use by an administrator user, and (B) a user interface for use by a user of a messaging system.

13. The method of claim 1, wherein the processing and associating are performed by one or more computing node remote and external from the computer device.

14. A computer program product comprising:
a computer readable storage medium readable by one or more processing unit and storing instructions for execution by one or more processor for performing a method comprising:
obtaining speech based message data and biometric data of a speaker user of a messaging system, the speech based message data being input into a computer device by the speaker user and the biometric data indicating one or more aspect of a physical condition of the speaker user during the input of the speech based message data into the computer device;
processing data to determine a truthfulness parameter of the speech based message data, the processing data to determine a truthfulness parameter including processing the biometric data, the truthfulness parameter indicating a probability that the speech based message data is knowingly untruthful; and
associating the truthfulness parameter to the speech based message data, wherein the associating includes tagging the speech based message data with the truthfulness parameter, wherein the processing includes performing a preliminary truthfulness determining process, the preliminary truthfulness determining process based on examining of biometric data, and wherein the processing includes performing a fact check process to determine factual correctness of content of the message data conditionally on the condition that the preliminary truthfulness determining process satisfies a criteria.

15. The computer program product of claim 14, wherein the method includes activating a speech Natural Language Processing (NLP) process to determine a sentiment parameter of the message data, and wherein the method includes tagging the message data with the sentiment parameter.

16. The computer program product of claim 14, wherein the processing includes determining the truthfulness parameter based each of the following (a) a biometric output for the message data, (b) a fact check process output, wherein the fact check process checks factual correctness of statements of the message data, and (c) an NLP process output, wherein the NLP process is performed on the message data.

17. The computer program product of claim 14, wherein the method includes performing a machine learning process for identifying signature behavior patterns for the user, the signature behavior patterns identified by the performing a machine learning process including signature behavior patterns identified as being exhibited by the user on input of message data that satisfies a criteria, and wherein the processing includes examining NLP output data for the speech based message data to determine whether a signature NLP pattern of the signature NLP patterns is included in the NLP output data.

18. The method of claim 14, wherein the processing includes determining the truthfulness parameter based on each of the following (a) received image data, (b) received blood pressure data, (d) received pulse data, (e) received skin conductivity data, and (f) received breathing data.

19. A system comprising:
a memory;
at least one processor in communication with the memory; and program instructions executable by one or more processor via the memory to perform a method comprising:
obtaining speech based message data and biometric data of a speaker user of a messaging system, the speech based message data being input into a computer device by the speaker user and the biometric data indicating one or more aspect of a physical condition of the speaker user during the input of the speech based message data into the computer device;
processing data to determine a truthfulness parameter of the speech based message data, the processing data to determine a truthfulness parameter including processing the biometric data, the truthfulness parameter indicating a probability that the speech based message data is knowingly untruthful; and
associating the truthfulness parameter to the speech based message data, wherein the associating includes tagging the speech based message data with the truthfulness parameter, wherein the processing includes performing a preliminary truthfulness determining process, the preliminary truthfulness determining process based on examining of biometric data, and wherein the processing includes performing a fact check process to determine factual correctness of content of the message data conditionally on the condition that the preliminary truthfulness determining process satisfies a criteria.

* * * * *